United States Patent [19]

Godfrey et al.

[11] Patent Number: 4,889,930

[45] Date of Patent: Dec. 26, 1989

[54] PROCESS FOR MAKING 2-OXO-1-((SUBSTITUTED SULFONYL)AMINO)CARBONZYL)AZETIDINES AND INTERMEDIATES USED THEREIN

[75] Inventors: Jollie D. Godfrey, Trenton; Richard H. Mueller, Ringoes; Robert Zahler, Princeton, all of N.J.

[73] Assignee: E. R. Squibb & Sons, Inc., Princeton, N.J.

[21] Appl. No.: 135,802

[22] Filed: Dec. 21, 1987

[51] Int. Cl.[4] .................. C07D 705/08; C07D 401/12; C07D 417/14; C07B 51/00
[52] U.S. Cl. ..................................... 540/363; 540/364
[58] Field of Search ............................... 540/363, 364

[56] References Cited

U.S. PATENT DOCUMENTS 4,743,685  5/1988  Brewer ................................. 540/363

Primary Examiner—Mark L. Berch
Attorney, Agent, or Firm—Theodore R. Furman, Jr.

[57] ABSTRACT

An improved process for making compounds having the formula

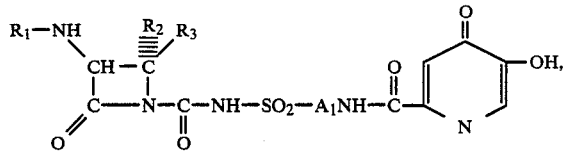

14 Claims, No Drawings

PROCESS FOR MAKING 2-OXO-1-((SUBSTITUTED SULFONYL)AMINO)CARBONZYL)AZETIDINES AND INTERMEDIATES USED THEREIN

FIELD OF THE INVENTION

The present invention relates to an improved process for the preparation of 2-oxo-1-[[(substituted sulfonyl)-amino]carbonyl]azetidines and, additionally, is directed to novel intermediates employed in such a process.

BACKGROUND OF THE INVENTION

Copending application Ser. No. 907,441, filed on September 15, 1986, describes 2-oxo-1-[[(substituted sulfonyl)-amino]carbonyl]azetidines having antibacterial activity. These azetidines can be characterized by the general formula

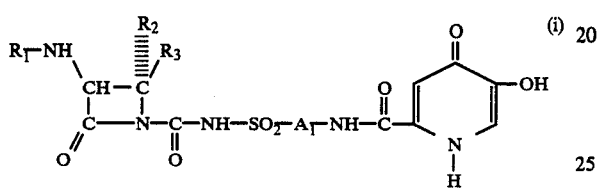

wherein $A_1$ represents various amino groups and substituted N-heterocyclic groups. Preferred compounds, as disclosed by the application, are [[[[[(1,4-dihydro-5-hydroxy-4-oxo-2-pyridinyl)carbonyl]amino]-2-oxo-imidazolidinyl]sulfonyl]amino]carbonyl-2-oxo-azetidines having the formula

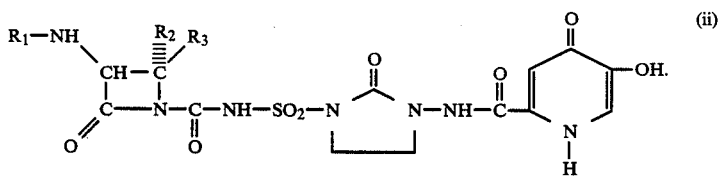

Several processes for preparing the above compounds are described. In one process, protected β-lactams of the formula

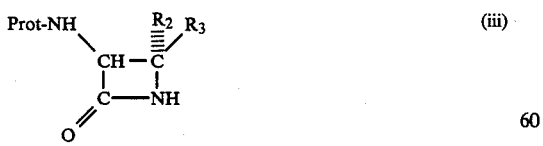

(wherein Prot is an amino protecting group such as benzyloxycarbonyl, t-butoxycarbonyl, trityl and the like) are reacted with an isocyanate of the formula

(iv)  O=C-
=N-SO-
2-Y, wherein Y is a leaving group such as chlorine, to provide intermediates of the formula

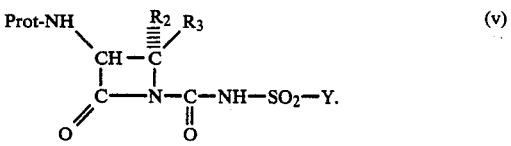

The Y leaving group can be displaced by reaction of a compound of formula (v) with the nucleophile of the formula

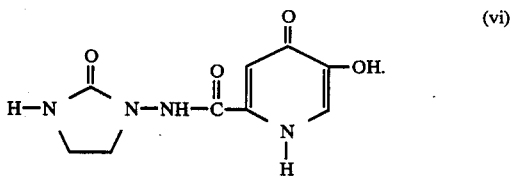

for example, in the case where $A_1$ of formula (i) is

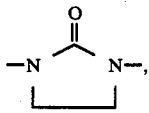

typically in the presence of a base, to provide intermediates of the formula

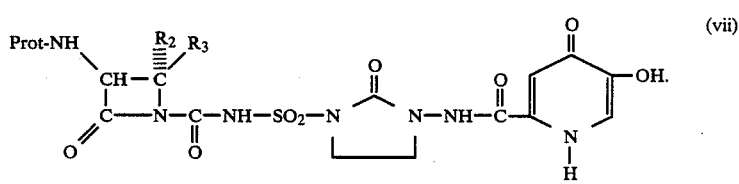

Deprotection and acylation are described to couple the desired $R_1$ moiety at the 3-amino site.

Alternatively, β-lactams other than compound (iii) are described as suitable for coupling with the isocyanate (iv) and acylation may be carried out at other points in the process.

To prepare the compound of formula (vi), a compound of the formula

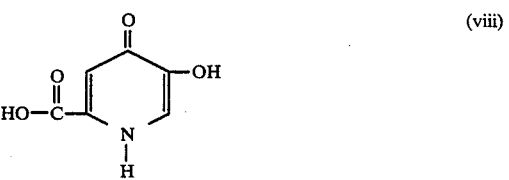

is provided with hydroxyl group protection followed by carboxyl activation and reacted with a compound of the formula

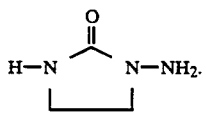

The so-formed compound (vi) is thereafter temporarily protected for coupling with compound (v) and then must be reprotected for the acylation to add $R_1$.

In scaling up this process for the purpose of manufacturing the compounds of formula (i), the numerous protection, deprotection and reprotection steps necessary in the described process render it costly and less efficient than preferred. Additionally, it has been found that because of the extremely water soluble nature of compound (ix) (and other H—$A_1$—$NH_2$ intermediates), its isolation for use in the described process is very difficult.

A more efficient process for making the compounds of formula (i) has been sought.

SUMMARY OF THE INVENTION

In accordance with the present invention a novel process is disclosed which is useful for making antibacterial compounds having the formula

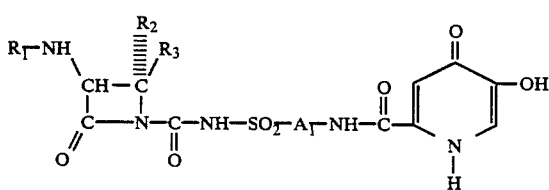

or pharmaceutically acceptable salts thereof wherein $A_1$ is

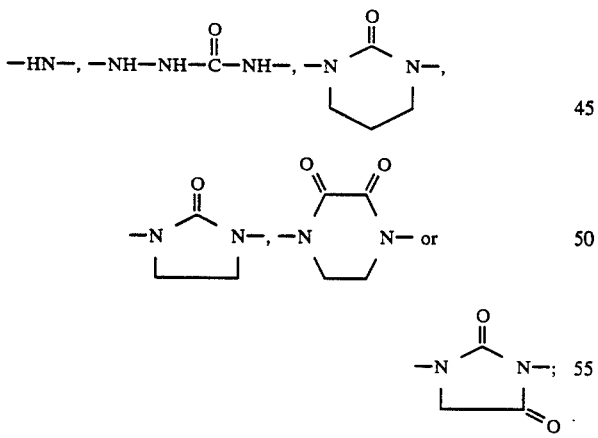

$R_1$ is an acyl group derived from a carboxylic acid; and, $R_2$ and $R_3$ are the same or different and each is hydrogen, alkyl, cycloalkyl, phenyl, substituted phenyl or a 4, 5, 6 or 7-membered heterocycle (hereinafter referred to as $R_x$), or one of $R_2$ and $R_3$ is hydrogen and the other is halomethyl, dihalomethyl, trihalomethyl, alkoxycarbonyl, carboxyl, —$CH_2X_1$ [wherein $X_1$ is amino (—$NH_2$), hydroxy, carboxyl, alkoxycarbonyl, alkanoylamino, phenylcarbonylamino, (substituted phenyl)carbonylamino, alkylsulfonyloxy, phenylsulfonyloxy, (substituted phenyl)sulfonyloxy, phenyl, substituted phenyl, cyano,

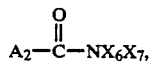

or —O—$X_2$ (wherein $A_2$, $X_2$, $X_6$ and $X_7$ are as hereinafter defined)], or —O—$X_2$ [wherein $X_2$ is alkyl, substituted alkyl, phenyl, substituted phenyl, phenylalkyl, (substituted phenyl)alkyl, alkanoyl, phenylalkanoyl, (substituted phenyl)alkanoyl, phenylcarbonyl, (substituted phenyl)carbonyl, or heteroarylcarbonyl],

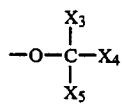

[wherein one of $X_3$ and $X_4$ is hydrogen and the other is hydrogen or alkyl, or $X_3$ and $X_4$ when taken together with the carbon atom to which they are attached form a cycloalkyl group; and $X_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl

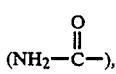

(substituted amino) carbonyl, or cyano (—C≡N)], or

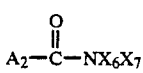

[wherein $A_2$ is —$(CH_2)_m$—, —$(CH_2)_m$—O—, or —$(CH_2)_m$—NH, m is 0, 1 or 2, and $X_6$ and $X_7$ are the same or different and each is hydrogen, alkyl, phenyl or substituted phenyl, or $X_6$ is hydrogen and $X_7$ is amino, substituted amino, alkanoylamino or alkoxy, or $X_6$ and $X_7$ when taken together with the nitrogen atom to which they are attached form a 4, 5, 6 or 7-membered heterocycle].

The present process, comprises treating a salt of the formula

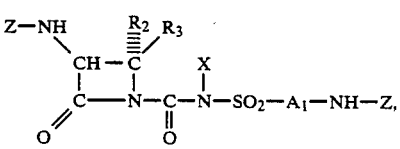

(wherein Z is benzyloxycarbonyl and X is selected from hydrogen, alkali earth metals and tri- or tetra-alkylammonium (TA) groups) in the presence of a ketonic solvent having the formula

(wherein R and R' are each alkyl or R and R' taken together with the carbon atom to which they are attached are 5-, 6- or 7-membered cycloalkyl) with hydrogen in the presence of a catalyst, followed by acylation to provide a compound having the formula

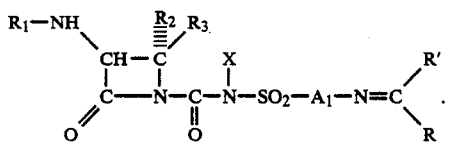

Following removal of the

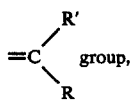

compound IV is reacted with a compound of the formula

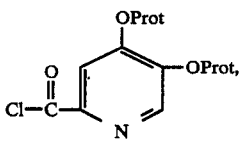

wherein Prot is a protecting group, and the resulting product is deprotected to provide the compounds of formula I.

Also in accordance with the present invention, novel intermediates are disclosed.

Detailed Description of the Invention

The β-lactams of formula I, and pharmaceutically acceptable salts thereof, have activity against gram-positive and gram-negative organisms. These compounds can be used as agents to combat bacterial infections (including urinary tract infections and respiratory infections) in mammalian species, such as domesticated animals (e.g. dogs, cats, cows, horses, and the like) and humans.

For combating bacterial infections in mammals, a compound of formula I can be administered to a mammal in need thereof in an amount of about 1.4 mg/kg/day to about 350 mg/kg/day, preferably about 14 mg/kg/day to about 100 mg/kg/day. All modes of administration which have been used in the past to deliver penicillins and cephalosporins to the site of the infection are also contemplated for use with β-lactams of this invention. Such methods of administration include oral, intravenous, intramuscular, and as a suppository.

The compounds produced by the process of this invention form basic salts with various inorganic and organic bases which are also within the scope of this invention. Such salts include ammonium salts, alkali metal salts, alkaline earth metal salts, salts with organic bases, e.g. dicyclohexylamine, benzathine, N-methyl-D-glucamine, hydrabamine and the like. The pharmaceutically acceptable salts are preferred, although other salts are also useful, e.g. in isolating or purifying the product.

Some of the compounds produced by the process of this invention may be crystallized or recrystallized from solvents containing water. In these cases, water of hydration may be formed. This invention contemplates stoichiometric hydrates as well as compounds containing variable amounts of water that may be produced by processes such as lyophilization.

The β-lactams of formula I contain at least one chiral center--the carbon atom in the 3-position of the β-lactam nucleus to which the acylamino substitutent ("$R_1$—NH—") is attached. This invention is directed to a process for producing those β-lactams which have been described above, wherein the stereochemistry at the chiral center in the 3-position of the β-lactam nucleus is the same as the configuration at the carbon atom in the 6-position of naturally occurring penicillins (e.g. penicillin G) and as the configuration at the carbon atom in the 7-position of naturally occurring cephamycins (e.g. cephamycin C). Also included within the scope of this invention are racemic mixtures which contain the above-described β-lactams.

Listed below are definitions of various terms used to describe the β-lactams produced by the process of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 10 carbon atoms are preferred.

The terms "cycloalkyl" and "cycloalkenyl" refer to cycloalkyl and cycloalkenyl groups having 3, 4, 5, 6 or 7 carbon atoms.

The term "substituted alkyl" refers to alkyl groups substituted with one or more (preferably 1, 2 or 3) azido, amino ($-NH_2$), halogen, hydroxy, carboxy, cyano, alkoxycarbonyl, aminocarbonyl, alkanoyloxy, alkoxy, phenyloxy, (substituted phenyl)oxy, alkylsulfinyl, or alkylsulfonyl groups.

The terms "alkanoyl", "alkenyl", and "alkynyl" refer to both straight and branched chain groups. Those groups having 2 to 10 carbon atoms are preferred.

The terms "halogen" and "halo" refer to fluorine, chlorine, bromine and iodine.

The term "substituted phenyl" refers to a phenyl group substituted with 1, 2 or 3 amino ($-NH_2$), halogen, hydroxyl, trifluoromethyl, alkyl (of 1 to 4 carbon atoms), alkoxy (of 1 to 4 carbon atoms), alkanoyloxy, aminocarbonyl, or carboxy groups.

The expression "a 4, 5, 6 or 7-membered heterocycle" (referred to as "$R_x$") refers to substituted and unsubstituted, aromatic and non-aromatic groups containing one or more (preferably 1, 2 or 3) nitrogen or oxygen atoms. Exemplary substituents are oxo ($=O$), halogen, hydroxy, nitro, amino, cyano, trifluoromethyl, alkyl of 1 to 4 carbons, alkoxy of 1 to 4 carbons, alkylsulfonyl, phenyl, substituted phenyl 2-furfurylideneamino

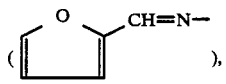

benzylideneamino and substituted alkyl groups (wherein the alkyl group has 1 to 4 carbons). One type of "4, 5, 6 or 7-membered heterocycle" is the "heteroaryl" group. The term "heteroaryl" refers to those 4, 5, 6 or 7-membered heterocycles which are aromatic. Exemplary heteroaryl groups are substituted and unsubstituted pyridinyl, furanyl, pyrrolyl, 1,2,3-triazolyl, 1,2,4-triazolyl, imidazolyl, pyrimidinyl, oxazolyl, triazinyl, and tetrazolyl. Exemplary nonaromatic heterocycles (i.e. fully or partially saturated heterocyclic groups) are substituted and unsubstituted azetidinyl, oxetanyl, piperidinyl, piperazinyl, imidazolidinyl, oxazolidinyl, pyrrolidinyl, tetrahydropyrimidinyl and hexahydroazepinyl. Exemplary of the substituted 4, 5, 6 or 7-membered heterocycles are 1-alkyl-3-azetidinyl, 2-oxo-1-imidazolidinyl, 3-alkylsulfonyl-2-oxo-1-imidazolidinyl, 3 benzylideneamino-2-oxo-1-imidazolidinyl, 3-alkyl-2-oxo-1-imidazolidinyl, 3-phenyl (or substituted phenyl)-2-oxo-1-imidazolidinyl, 3-benzyl-2-oxo-1-imidazolidinyl, 3-(2-aminoethyl)-2-oxo-1-imidazolidinyl, 3-amino-2-oxo-1-imidazolidinyl, 3-[(alkoxycarbonyl)amino]-2-oxo-1-imidazolidinyl, 3-[2-[(alkoxycarbonyl)amino]ethyl]-2-oxo-1-imidazolidinyl, 2-oxo-1-pyrrolidinyl, 2-oxo-3-oxazolidinyl, 4-hydroxy-6-methyl-2-pyrimidinyl, 2-oxo-1-hexahydroazepinyl, 2-oxo-3-pyrrolidinyl, 2-oxo-3-tetrahydrofuranyl, 2,3-dioxo-1-piperazinyl, 2,5-dioxo-1-piperazinyl, 4-alkyl-2,3-dioxo-1-piperazinyl, and 4-phenyl-2,3-dioxo-1-piperazinyl.

The term "substituted amino" refers to a group having the formula —NX$_8$X$_9$ wherein X$_8$ is hydrogen, alkyl, phenyl, substituted phenyl, phenylalkyl or (substituted phenyl)alkyl, and X$_9$ is alkyl, phenyl, substituted phenyl, phenylalkyl, (substituted phenyl)alkyl, hydroxy, cyano, alkoxy, phenylalkoxy, or amino (—NH$_2$).

The term "acyl" refers to all organic radicals derived from an organic acid (i.e. a carboxylic acid) by removal of the hydroxyl group. Certain acyl groups are, of course, preferred but this preference should not be viewed as a limitation of the scope of this invention. Exemplary acyl groups are those acyl groups which have been used in the past to acylate β-lactam antibiotics including 6-aminopenicillanic acid and derivatives and 7-aminocephalosporanic acid and derivatives; see for example, Cephalosporins and Penicillins, edited by Flynn, Academic Press (1972), German Offenlegungsschrift 2,716,677, published Oct. 10, 1978, Belgian Pat. No. 867,994, published Dec. 11, 1978, U.S. Pat. No. 4,152,432, issued May 1, 1979, U.S. Pat. No. 3,971,778, issued July 27, 1976, U.S. Pat. No. 4,172,199, issued Oct. 23, 1979, and British Pat. No. 1,348,894, published Mar. 27, 1974. The portions of these references describing various acyl groups are incorporated herein by reference. The following list of acyl groups is presented to further exemplify the term "acyl"; it should not be regarded as limiting that term. Exemplary acyl groups are:

(a) Aliphatic groups having the formula

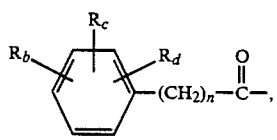

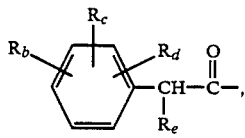

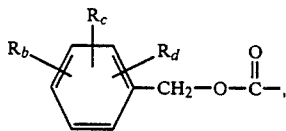

-continued

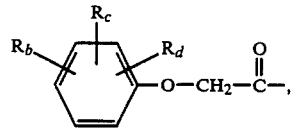

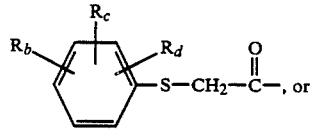

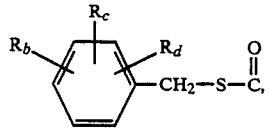

wherein R$_a$ is alkyl, cycloalkyl, alkoxy, alkenyl, cycloalkenyl, cyclohexadienyl, or alkyl or alkenyl substituted with one or more halogen, cyano, nitro, amino, mercapto, alkylthio, or cyanomethylthio groups;

(b) Carbocyclic aromatic groups having the formula

wherein n is 0, 1, 2 or 3; R$_b$, R$_c$ and R$_d$ each is independently hydrogen, halogen, hydroxyl, nitro, amino, cyano, trifluoromethyl, alkyl of 1 to 4 carbon atoms, alkoxy of 1 to 4 carbon atoms or aminomethyl; and R$_e$ is amino, hydroxyl, a carboxyl salt, protected carboxyl, formyloxy, a sulfo salt, a sulfoamino salt, azido, halogen, hydrazino, alkylhydrazino, phenylhydrazino, or [(alkylthio)thioxomethyl]thio;

Preferred carbocyclic aromatic acyl groups include those having the formula

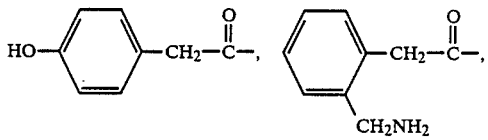

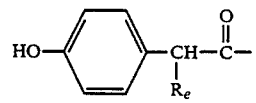

(R$_e$ is preferably a carboxyl salt or sulfo salt) and

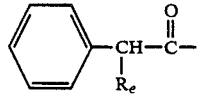

(R$_e$ is preferably a carboxyl salt or sulfo salt);

(c) Heteroaromatic groups having the formula

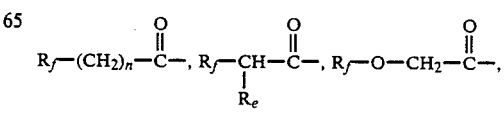

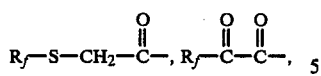

wherein n is 0, 1, 2 or 3; $R_e$ is as defined above; and $R_f$ is a substituted or unsubstituted 5-, 6- or 7-membered heterocyclic ring containing 1, 2, 3 or 4 (preferably 1 or 2) nitrogen, oxygen and sulfur atoms. Exemplary heterocyclic rings are thienyl, furyl, pyrrolyl, pyridinyl, pyrazolyl, pyrazinyl, thiazolyl, pyrimidinyl, thiadiazolyl and tetrazolyl. Exemplary substitutents are halogen, hydroxyl, nitro, amino, protected amino, cyano, trifluoromethyl, alkyl of 1 to 4 carbon atoms, alkoxy of 1 to 4 carbon atoms, or

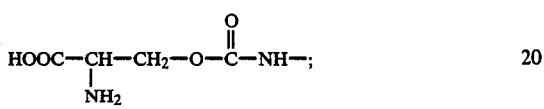

Preferred heteroaromatic acyl groups include those groups of the above formulas wherein $R_f$ is 2-amino-4-thiazolyl, 2-amino-5-halo-4-thiazolyl, 4-aminopyrimidin-2-yl, 5-amino-1,2,4-thiadiazol-3-yl, 2-thienyl, 2-furanyl, or 6-aminopyridin-2-yl;

(d) [[(4-Substituted-2,3-dioxo-1-piperazinyl)carbonyl]amino]arylacetyl groups having the formula

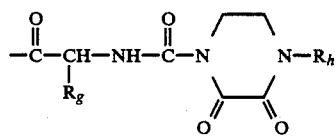

wherein $R_g$ is an aromatic group (including carbocyclic aromatics such as those of the formula

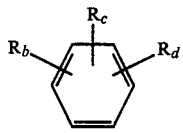

and heteroaromatics as included within the definition of $R_f$); and $R_h$ is alkyl, substituted alkyl (wherein the alkyl group is substituted with one or more halogen, cyano, nitro, amino or mercapto groups), arylmethyleneamino (i.e. —N=CH—$R_g$ wherein $R_g$ is as defined above), arylcarbonylamino (i.e.

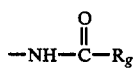

wherein $R_g$ is as defined above) or alkylcarbonylamino;

Preferred [[(4-substituted-2,3-dioxo-1-piperazinyl)carbonyl]amino]arylacetyl groups include those wherein $R_h$ is ethyl, phenylmethyleneamino or 2-furylmethyleneamino;

(e) (Substituted oximino)arylacetyl groups having the formula

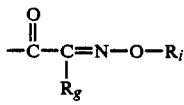

wherein $R_g$ is as defined above and $R_i$ is hydrogen, alkyl, cycloalkyl,

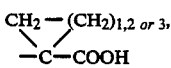

2-pyrrazolylmethyl, (2-oxo-3-pyrrolidinyl)methyl, alkylaminocarbonyl, arylaminocarbonyl (i.e.

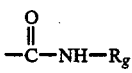

wherein $R_g$ is as defined above) or substituted alkyl (wherein the alkyl group is substituted with one or more halogen, cyano, nitro, amino, mercapto, alkylthio, aromatic group (as defined by $R_g$), carboxyl (including salts thereof), amido, alkoxycarbonyl, phenylmethoxycarbonyl, diphenylmethoxycarbonyl, hydroxyalkoxyphosphinyl, dihydroxyphosphinyl, hydroxy(phenylmethoxy)phosphinyl, dialkoxyphosphinyl or tetrazolyl substituents;

Preferred (substituted oxyimino)arylacetyl groups include those wherein $R_g$ is 2-amino-4-thiazolyl. Also preferred are those groups wherein $R_i$ is methyl, ethyl, carboxymethyl, 1-carboxy-1-methylethyl, 2,2,2-trifluoroethyl or 1-carboxycyclopropyl;

(f) (Acylamino)arylacetyl groups having the formula

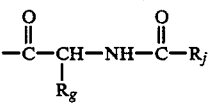

wherein $R_g$ is as defined above and $R_j$ is

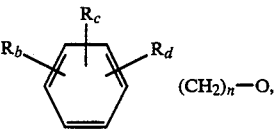

amino, alkylamino, (cyanoalkyl)amino, amido, alkylamido, (cyanoalkyl)amido,

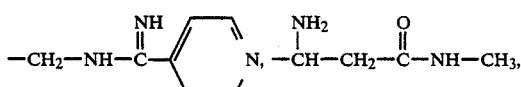

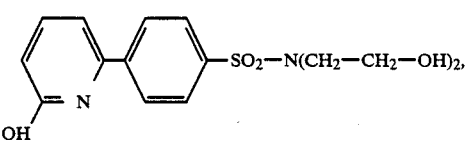

-continued

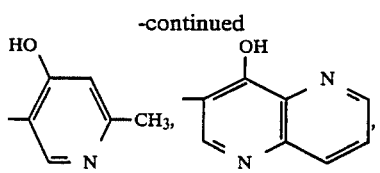

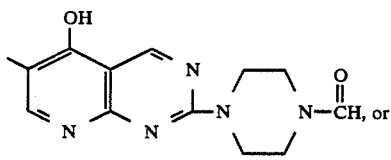

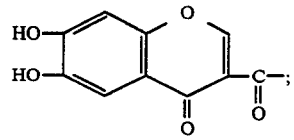

Preferred (acylamino)arylacetyl groups of the above formula include those groups wherein $R_j$ is amino or amido. Also preferred are those groups wherein $R_g$ is phenyl or 2-thienyl;

(g) [[[3-Substituted-2-oxo-1-imidazolidinyl]carbonyl-]amino]arylacetyl groups having the formula

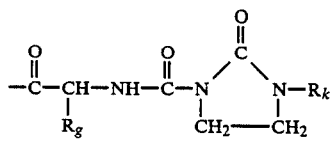

wherein $R_g$ is as defined above and $R_k$ is hydrogen, alkylsulfonyl, arylmethyleneamino (i.e. —N=CH—$R_g$ wherein $R_g$ is as defined above),

—C—$R_m$ (wherein $R_m$ is hydrogen, alkyl or halogen substituted alkyl), aromatic group (as defined by $R_g$ above), alkyl or substituted alkyl (wherein the alkyl group is substituted with one or more halogen, cyano, nitro, amino or mercapto groups);

Preferred [[3-substituted-2-oxo-1-imidazolidinyl]carbonyl]amino]arylacetyl groups of the above formula include those wherein $R_g$ is phenyl or 2-thienyl. Also preferred are those groups wherein $R_k$ is hydrogen, methylsulfonyl, phenylmethyleneamino or 2-furylmethyleneamino.

The process for preparing the compounds of formula I, described in copending application Ser. No. 907,441 filed Sept. 15, 1986, has been improved.

In accordance with the present invention, the β-lactams of formula I can be prepared by first reacting a 3-protected amino-2-azetidinone having the formula

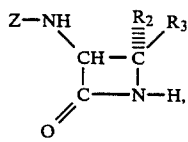

wherein Z is benzyloxycarbonyl, with an isocyanate having the formula

VII          O=C=N—SO₂—Y, wherein Y is a leaving group, such as chlorine, in the presence of an inert organic solvent, e.g. ethyl acetate, tetrahydrofuran, dimethoxyethane, dichloromethane, acetonitrile or mixtures thereof, as disclosed in copending application Ser. No. 907,441, filed Sept. 15, 1986.

Reaction, thereafter, with an intermediate of the formula

VIII          H—A₁—NH—Z, in the presence of a tertiary alkylamine, e.g. triethylamine or diisopropylethylamine, and a solvent, such as dichloromethane, provides the novel intermediate of the formula

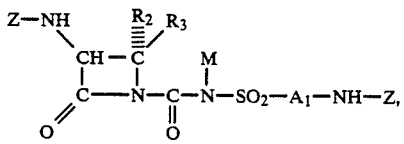

that is, the compounds of formula II wherein X is M and wherein M is hydrogen or an alkali earth metal, e.g. calcium or sodium.

Preferably, compound IX is treated with a tri- or tetra-alkylammonium (TA) sulfate, e.g. tetrabutylammonium sulfate, to provide the TA salt of the formula

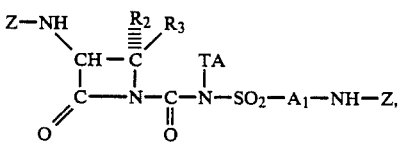

that is, the compounds of formula II wherein X is TA.

The novel bis-Z protected intermediates of formula II below

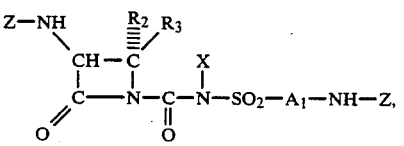

are considered part of the present invention.

A salt of formula II, i.e. the M salt of formula IX or preferably the TA salt of formula X, in a solvent, e.g. methylene chloride, and in the presence of a ketonic solvent of the formula

is reduced, for example, with hydrogen in the presence of a catalyst such as palladium on carbon. The preferred ketonic solvents of formula III include acetone, diethyl ketone and methyl ethyl ketone. This is followed immediately by acylation of the salt and treatment with trifluoroacetic acid in methanol to provide

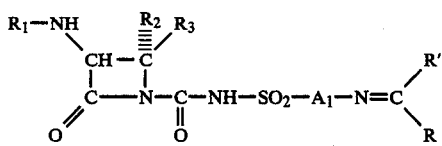 XI

A key to the process described above is that the salt

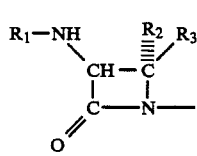

of formula II is deprotected at both the 3-amino- and the imidazolidinyl amino sites and immediately thereafter is selectively reprotected at the imidazolidinyl amino site with the alkylidine group,

before the acylation by reaction with the ketonic solvent. Without this selective in situ reprotection, acylation would be expected to occur at both ends of the molecule.

Well known acylation techniques can be used to convert an intermediate of formula II (that is, intermediates IX or X) to a corresponding intermediate of formula XI. Exemplary techniques include reaction of a compound of formula II, treated as described above, with a carboxylic acid (R₁—OH), or corresponding carboxylic acid halide or carboxylic acid anhydride. The reaction should preferably take place in the presence of diisopropylethylamine. Optionally, the reaction with a carboxylic acid will proceed in the presence of a carbodiimide such as dicyclohexylcarbodiimide and a substance capable of forming an active ester in situ such as N-hydroxybenzotriazole. In those instances where the acyl group (R₁) contains reactive functionality (such as amino or carboxyl groups) it may be necessary to first protect those functional groups, then carry out the acylation reaction, and finally deprotect the resulting product.

Preferably, compound XI can be treated with an alkoxyamine, or O-benzylhydroxylamine, in the presence of a tertiary amine, e.g. diisopropylethylamine, and pyridinium p-toluene sulfonate in an organic solvent, e.g. methylene chloride or acetonitrile, to remove

This is immediately followed by reaction with an intermediate of the formula

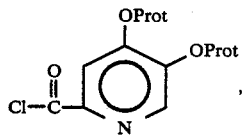 XII wherein Prot is a protecting group other than benzyl, such as t-butoxycarbonyl or typical phenol protecting groups, e.g. acetates, benzoates and pivalates, to provide a compound of the formula

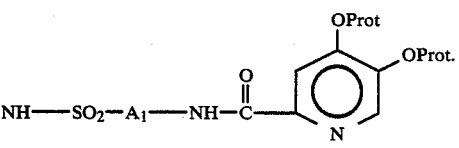 XIII

Alternatively, compound XI can be treated with a mild aqueous acid, such as sodium hydrogen phosphate, in the presence of an organic solvent, such as acetonitrile, to provide a compound of the formula

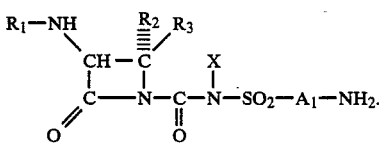 XIV

Compound XIV can thereafter be reacted with compound XII above to provide the compounds of formula XIII.

Compound XIII is thereafter deprotected to form the compounds of formula I, or salts thereof, by techniques known in the art, such as by treatment with trifluoroacetic acid.

The intermediates of formula XII can be prepared by treating a compound of the formula

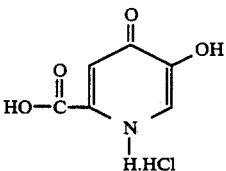 XV with benzyl alcohol in the presence of a solvent, e.g. cyclohexane, and a strong acid, e.g. p-toluenesulfonic acid, to provide

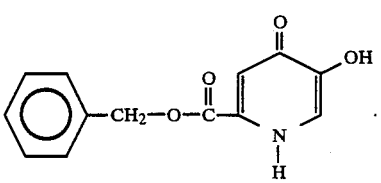 XVI

Compound XVI in a solvent, e.g. methylene chloride, can be reacted with (Prot)₂·O  XVII or with a compound having the formula

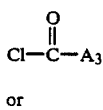

XVIIIa or

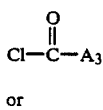

XVIIIb (wherein $A_3$ is alkyl, cycloalkyl or phenyl) in the presence of an acetylation catalyst, such as dimethylaminopyridine, to provide the compound

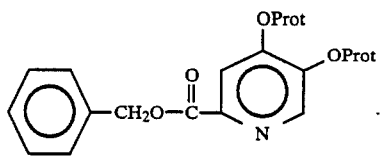

XIX

Reduction of compound XIX, such as by treating with hydrogen in the presence of a catalyst, such as palladium on carbon, in a solvent, such as methylene chloride, provides a compound of the formula

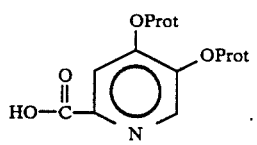

XX

Preferably, "Prot" is t-butoxy carbonyl (BOC) to provide a preferred and novel intermediate

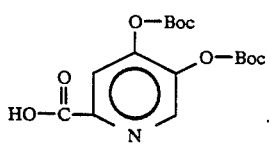

XXa

Although the typical phenol protecting groups, i.e. acetates, benzoates and pivalates, are suitable for use on compound XX in the present process, it has been found that the deprotection process can cause some cleavage of the β-lactam ring resulting in lower yields. By using the bis-BOC protected acid of formula XXa, a higher yield is realized. This was unexpected since BOC is typically an amine protecting group.

Compound XX, in a solvent such as dichloromethane or acetonitrile in the presence of dimethylformamide as a catalyst, is thereafter treated with a chlorinating agent, e.g. oxalyl chloride, and pyridine to provide the intermediate of formula XII.

To make the intermediates of formula VIII, a compound of the formula $$H-A_1-H$$

XXI is treated with a nitrosating reagent, e.g. sodium nitrite in aqueous sulfuric acid, followed by reduction, e.g. by treatment with zinc, and thereafter reacted with a compound of the formula halogen—Z

XXII followed by treatment with an acid, e.g. hydrochloric.

The present process is particularly suitable for preparation of the preferred compounds of formula I wherein $A_1$ is

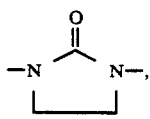

that is,

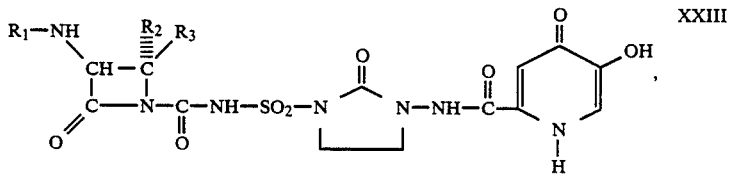

XXIII in which case compound VIII in the above reactions is represented by

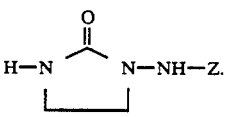

XXIV

The preparation of the unprotected form of compound XXIV has been described (Michels and Gever, J. Amer. Chem. Soc., 1956, 78, 5349), and this unprotected form was used in copending application Ser. No. 907,441. However, due to the extreme water solubility of the unprotected form, its isolation is extremely difficult. The protected intermediate XXIV used in the present process is prepared by treating a compound of the formula

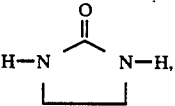

XXV in suspension with sulfuric acid with sodium nitrite and then with zinc dust. Thereafter, the pH may be adjusted to between about 8.0 and 9.0, e.g. with sodium hydroxide, and the so-treated compound is reacted with a compound of formula XXII and then treated with an acid, e.g. hydrochloric, to provide the intermediate of formula XXIV. The benzyloxycarbonyl-protected compound of formula XXIV is much less soluble in water than the unprotected form and therefore its isolation is substantially easier.

The process of the present invention is particularly useful for preparation of the product of formula I wherein $R_1$ is

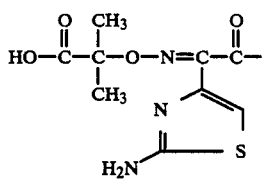

or the disodium salt thereof, and wherein $R_2$ and $R_3$ are each hydrogen, that is, the compound having the formula

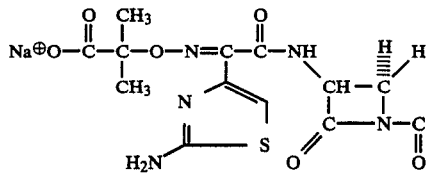

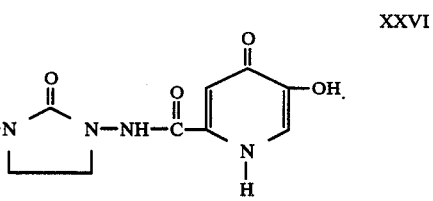

The present invention will now be described by reference to the following examples, however, it is not meant to be limited to the details therein.

EXAMPLE 1

2-[[[1-(2-Amino-4-thiazolyl)-2-[[1-[[[[3-[[(1,4-dihydro-5-hydroxy-4-oxo-2-pyridinyl)carbonyl]amino]-2-oxo-1-imidazolidinyl]sulfonyl]amino]carbonyl]-2-oxo-3-azetidinyl]amino]-2-oxoethylidene]amino]oxy-2-methylpropanoic acid, disodium salt

A. (2-Oxo-1-imidazolidinyl)carbamic acid, phenylmethyl ester

To a suspension of imidazolidinone (252 g, 2.98 mole) and 2N hydrogen sulfate (4 l) at 0° C. was added sodium nitrite (101 g, 1.46 mole) portionwise over 15 minutes while maintaining a reaction temperature of 1° C. After the addition was complete the suspension was stirred 2.5 hours at 0° C.

The 0° C. mixture was then treated with zinc dust (220 g, 3.36 mole) in small portions over 1 hour not letting the reaction temperature exceed 5° C. The resulting mixture was stirred at 0° C. for 30 minutes, the cold bath was removed and the reaction stirred 3 hours longer at room temperature. The mixture was filtered through a pad of Celite to remove excess zinc, and the Celite was washed with water (500 ml).

The colorless filtrate was taken to pH 8.50 with the addition of 25% aqueous sodium hydroxide forming a thick colorless suspension. Benzyl chloroformate (208 g, 1.45 mole) was added and the pH was maintained at 8.50–9.0 with the addition of the sodium hydroxide solution. After 1 hour an additional portion of benzyl chloroformate (20 ml, 0.14 mole) was added and the pH was maintained at 8.50 with the addition of the sodium hydroxide solution. After stirring for an additional 2 hours, the reaction mixture was adjusted to pH 2.0 by the addition of aqueous hydrochloric acid (concentrated hydrochloric acid:water, 1:1). The reaction mixture was cooled to 18° C. and then filtered to obtain a colorless solid. This material was washed with water (2.5 l) then with ether (800 ml), and air dried to give 283 g of the crude title A compound. Recrystallization from acetonitrile (900 ml) followed by recrystallization from methanol (550 ml) gave 220 g of the final title A compound.

B. (S)-[2-Oxo-1-[[[[2-oxo-3-[[(phenylmethoxy)carbonyl]amino]-1-imidazolidinyl]sulfonyl]amino]carbonyl]-3-azetidinyl]carbamic acid, phenylmethyl ester, monosodium salt To a stirred suspension of (S)-(2-oxo-3-azetidinyl)carbamic acid, phenylmethyl ester (2 g, 9.08 mmol) in ethyl acetate (60 mL) at −30° C. under argon was added chlorosulfonyl isocyanate (0.80 mL, 9.19 mmol). The resulting mixture was stirred at −30° C. and the suspension gradually clears to give a colorless solution. After 1 hour at −30° C., dichloromethane (30 mL) was added followed by compound A (2.24 g, 9.52 mmol). To the resulting suspension at −30° C. was added dropwise over 15 minutes a solution of diisopropylethylamine (3.16 mL, 18.14 mmol) in dichloromethane (30 mL). Dichloromethane (6 mL) was used to rinse the addition funnel. The reaction was then allowed to warm to room temperature. After stirring overnight, the reaction mixture (pale yellow) was washed with dilute hydrogen sulfate (30 mL) and water. After drying over anhydrous magnesium sulfate, the solvent was removed at reduced pressure to give a pale yellow oil. This material was dissolved in acetone (40 mL) and water (20 mL). The resulting solution (pH∼2-3) was adjusted to pH 6.5 by the addition of 1N sodium hydroxide. The resulting solution was seeded and the acetone was slowly removed at reduced pressure. The resulting slurry was filtered and the solid was washed with water, absolute ethanol, and with ether (to aid in drying). After drying under vacuum over phosphorus pentoxide, 4.41 g of the title B compound was obtained as a colorless solid, m.p. 220° C.

C. (S)-[2-Oxo-1[[[[2-oxo-3-[[(phenylmethoxy)carbonyl]amino]-1-imidazolidinyl]sulfonyl]amino]carbonyl]-3-azetidinyl]carbamic acid, phenylmethyl ester 1.0 tetrabutylammonium salt A solution of tetrabutylammonium hydrogen sulfate (6 g, 17.67 mmol) in water (60 mL) was adjusted to a pH of 3.5 by the addition of 1N sodium hydroxide. This solution was then added to dichloromethane (300 mL) followed by the addition of the title B compound (10 g, 17.17 mmol). After stirring vigorously for 30 minutes, the dichloromethane layer was separated and washed with water. After drying over anhydrous magnesium sulfate, the solvent was removed at reduced pressure to afford a foam which when crushed affords 13.49 g of the title C compound as a dense solid, m.p. 75.7°–116.3° C.

Analysis calc'd for $C_{39}H_{59}N_7O_9S.0.03CH_2Cl_2$: C, 58.27; H, 7.40; N, 12.19; S, 3.99; Cl 0.26;

Found: C, 57.94; H, 7.33; N, 12.15; S, 4.05; Cl, 0.20.

D.
(S)-2-[[[1-(2-Amino-4-thiazolyl)-2-[[1-[[[[3-[(1-methylethylidene)amino]-2-oxo-1-imidazolidinyl]sulfonyl]amino]carbonyl]-2-oxo-3-azetidinyl]amino]-2-oxoethylidene]amino]oxy]-2-methylpropanoic acid, diphenylmethyl ester A mixture of the title C compound (10 g, 12.47 mmol) and 10% palladium on carbon (1 g) in dichloromethane (80 mL), acetone (40 mL), and water (0.5 mL) was stirred under a hydrogen atmosphere with a continuous flow of hydrogen through the reaction vessel. Additional solvent was added during the reaction to replace that lost by the hydrogen purge. After 3 hours, chromatography analysis showed the reaction to be complete and the reaction vessel was purged with argon. To the resulting mixture was added (Z)-2-amino-α-[[2-(diphenylmethoxy)-1,1-dimethyl-2-oxoethoxy]imino]-4-thiazoleacetic acid, 1H-benzotriazol-1-yl ester (6.94 g, 12.47 mmol) followed by diisopropylethylamine (2.17 mL, 12.47 mmol). After stirring at room temperature under argon for 15 hours, the catalyst was removed by filtration through Celite and the Celite bed was washed with dichloromethane. The filtrate was concentrated at reduced pressure and the residue was dissolved in dichloromethane (~600 mL). The resulting solution was washed with pH 4.0 phosphate buffer and pH 7.0 phosphate buffer. After drying over anhydrous magnesium sulfate, the solvent was removed at reduced pressure. The resulting viscous yellow oil was then placed under vacuum for ~3 hours to give a yellow foam. This foam was dissolved in methanol (65 mL). To the resulting solution was added trifluoroacetic acid (1 mL, 12.98 mmol, 1.04 eq) dropwise over ~1 minute. After ~2 minutes, the solution became cloudy and a precipitate began to form. After stirring for 1 hour at room temperature, the mixture was cooled to 0° C. After stirring for 1 hour at 0° C., the product was collected by filtration and washed twice with ice cold methanol (15 mL). The material was then dried under vacuum over phosphorus pentoxide to afford 8.33 g of the title D compound as an off-white granular solid, m.p. 165° C.

Analysis calc'd for $C_{32}H_{35}N_9O_9S_2 \cdot 1.2$ m $H_2O$: C, 49.57; H, 4.86; N, 16.26; S, 8.27; F, 0.00; KF, 2.8;

Found: C, 49.54; H, 4.58; N, 15.92; S, 8.47; F, 0.00; KF, 2.8.

E. 1,4-Dihydro-5-hydroxy-4-oxo-2-pyridinecarboxylic acid, phenylmethyl ester A vessel equipped with a water separator was charged with 1,4-dihydro-5-hydroxy-4-oxo-2-pyridine carboxylic acid monohydrochloride (100 g, 0.52 mole), p-toluenesulfonic acid (123.5 g, 0.65 mole), benzyl alcohol (1000 ml) and cyclohexane (625 ml). The resulting mixture was refluxed for 24 hours during which 68 ml of water was collected. The heterogeneous mixture was cooled (~50° C.) and cyclohexane (725 ml) was added. After stirring for 1 hour at ambient temperature, the solid was filtered, washed with 20% cyclohexane in ethyl acetate (1000 ml) and dried to give 207 g of a white solid. This material was suspended in ice cold water (1200 ml) and the pH was adjusted to 8.0 with the addition of 15% sodium hydroxide solution (~150 ml). After stirring for 1 hour the material was collected by filtration, washed with water (1000 ml), and dried to give 107.1 g of the title E compound as a colorless solid, m.p. 115° C. (dec).

Analysis calc'd for $C_{13}H_{11}NO_4 \cdot 0.11M$ $H_2O$: C, 63.16; H, 4.57; N, 5.67; KF, 0.80;

Found: C, 63.37; H, 4.60; N, 5.69; KF, 0.77.

F.
4,5-Bis[[(1,1-dimethylethoxy)carbonyl]oxy]-2-pyridinecarboxylic acid, phenylmethyl ester To a suspension of crude title E compound (1.40 g, 5.71 mmol) in dry dichloromethane (30 mL) at room temperature under argon was added 4-dimethylaminopyridine (100 mg, 0.82 mmol, 0.14 eq) followed by di-tert-butyl dicarbonate (2.74 g, 2.2 eq). Vigorous gas evolution began almost immediately. After stirring for 15 minutes, an additional portion of di-tert-butyl dicarbonate (200 mg, 0.92 mmol, 0.16 eq) was added. After stirring for an additional 15 minutes, the reaction mixture was diluted with ether and washed twice with 0.2M phosphate buffer, 1N sodium hydrogen carbonate, and brine. After drying over anhydrous magnesium sulfate, the solvent was removed at reduced pressure to give a bright yellow oil. This material was combined with that obtained from another reaction (1 g) and chromatographed to afford 3.83 g of the title F compound as a viscous colorless oil.

Analysis calc'd for $C_{23}H_{27}NO_8 \cdot 0.25$ m $H_2O$: C, 61.39; H, 6.16; N, 3.11; KF, 1.00;

Found: C, 61.53; H, 6.19; N, 3.04; KF, 1.00.

G.
4,5-Bis[[(1,1-Dimethylethoxy)carbonyl]oxy]-2-pyridinecarboxylic acid

A mixture of the title F compound (~3.50 g, 6.85 mmol) and 10% palladium on carbon (300 mg) in dichloromethane (60 mL) was stirred under a hydrogen atmosphere. Chromatography analysis after 75 minutes shows the reaction to be essentially complete. The catalyst was removed by filtration through Celite over a Teflon millipore membrane (0.50μ) and filter bed washed with dichloromethane. The filtrate was concentrated at reduced pressure and the residue was chased twice with ether (10 mL). The residue was dissolved in ether (~7 mL) and seeded. After standing for ~15 minutes, the solvent was removed to afford 2.30 g of the title G compound as a colorless solid, m.p. 107° C.

Analysis calc'd for $C_{16}H_{21}NO_8$: C, 54.08; H, 5.96; N, 3.94;

Found: C, 54.31; H, 6.01; N, 3.87.

H.
4,5-Bis[[(1,1-Dimethylethoxy)carbonyl]oxy]-2-pyridinecarboxylic acid chloride A solution of the title G compound (1.920 g, 5.403 mmol) in dry dichloromethane (58 mL) under argon was cooled to 0° C. and to it was added N,N-dimethylformamide (0.0123 mL, 0.159 mmol) and pyridine (0.437 mL, 5.403 mmol). To the solution was added dropwise over 10 minutes distilled oxalyl chloride (0.486 mL, 5.571 mmol). Gas evolved rapidly during the addition. For 1 hour after addition was complete, a sweep of argon was maintained while the mixture was rapidly stirred to facilitate removal of residual gases. The resulting very pale blue solution was cooled further to −40° C. and maintained there.

I.

[3S(Z)]-2-[[[1-(2-Amino-4-thiazolyl)-2-[[1-[[[[3-[[[4,5-bis[[(1,1-dimethylethoxy)carbonyl]oxy]-2-pyridinyl]-carbonyl]amino]-2-oxo-1-imidazolidinyl]sulfonyl]amino]carbonyl]-2-oxo-3-azetidinyl]amino]-2-oxoethylidene]amino]oxy]-2-methylpropanoic acid, diphenylmethyl ester The title D compound (4.00 g, 5.307 mmol) was slurried in dry dichloromethane (76 ml) under argon. Addition of diisopropylethylamine (0.924 ml, 5.305 mmol) caused dissolution in 15 minutes. The nearly colorless solution was cooled to −20° C. and to it was added solid pyridinium p-toluenesulfonate (0.266 g, 1.06 mmol) which dissolved in 5 minutes. To the cold solution was then added dropwise O-benzylhydroxylamine (0.612 ml, 5.32 mmol) over 5 minutes. The resulting solution was stirred at −20° C. for one hour and then cooled to −40° C.

To the so-formed cold solution was added, via cannula over 10 minutes, the cold acid chloride solution formed in step H while −40° C. was maintained. Effluent acid chloride as it entered the coupling reaction vessel measured −33° C. and no exotherm in the reaction mixture was noticed. The nearly colorless reaction mixture was stirred at −40° C. for 45 minutes. Quench and workup was accomplished by pouring the cold reaction mixture into, and washing with, sodium phosphate buffer (pH 2.0, 0.2M, 2×100 mL). Layer separation was quick and each aqueous layer was back extracted with dichloromethane (10 mL). The combined cloudy, nearly colorless organic layers were dried over sodium sulfate, filtered, and reduced in vacuo to an oily solid. The compound was dissolved in ethyl acetate (24 mL) and precipitated by the slow addition of diethyl ether (40 mL) into the rapidly stirred solution, followed by the more rapid addition of ether (120 mL) to complete precipitation. Filtration, cake rinse (ether), and drying at ambient temperature under high vacuum produced 5.14 g of the slightly static-laden title I compound as a finely divided white powder, m.p. 198°–220° C.

Analysis calc'd for $C_{45}H_{50}N_{10}O_{16}S_2.0.42H_2O.0.05EtOAC.0.03 HCl$: C, 51.03; H, 4.86; N, 13.17; S, 6.03; Cl, 0.08; KF, 0.72;

Found: C, 50.93; H, 4.81; N, 13.07; S, 6.09; Cl, 0.08; KF 0.72.

J.

2-[[[1-(2-Amino-4-thiazolyl)-2-[[1-[[[[3-[[(1,4-dihydro-5-hydroxy-4-oxo-2-pyridinyl)carbonyl]amino]-2-oxo-1-imidazolidinyl]sulfonyl]amino]carbonyl]-2-oxo-3-azetidinyl]amino]-2-oxoethylidene]amino]oxy]-2-methylpropanoic acid, disodium salt To trifluoroacetic acid (40 ml) at −2° C. under argon was added anisole (16 ml). To this solution was added the title I compound (10.0 g, 9.51 mmol) over 5 minutes. The resulting mixture was stirred at −2° C. for 5 hours. The reaction mixture was diluted with ethyl acetate (80 ml) followed by the addition of cyclohexane (160 ml). After stirring for 5 minutes, the resulting suspension was filtered and the product cake was washed with ethyl acetate/cyclohexane (1:2, 2×50 ml), ethyl acetate/cyclohexane (1:1, 1×50 ml), and ethyl ether (2×25 ml). After drying, the product was suspended in water and the pH was adjusted to 6.0 by the addition of sodium bicarbonate. The resulting solution was then chromatographed on HP-20 to give the title compound after lyophilization.

EXAMPLE 2

2-[[[1-(2-Amino-4-thiazolyl)-2-[[1-[[[[3-[[(1,4-dihydro-5-hydroxy-4-oxo-2-pyridinyl)carbonyl]amino]-2-oxo-1-imidazolidinyl]sulfonyl]amino]carbonyl]-2-oxo-3-azetidinyl]amino]-2-oxoethylidene]amino]oxy]-2-methylpropanoic acid, disodium salt

A.

(S)-2-[[[1-(2-Amino-4-thiazolyl)-2-[[1-[[[[3-amino-2-oxo-1-imidazolidinyl]sulfonyl]amino]carbonyl]-2-oxo-3-azetidinyl]amino]-2-oxoethylidene]amino]oxy]-2-methylpropanoic acid, diphenylmethyl ester To a slurry of the title D compound from Example 1 (1.50 g, 1.99 mmol) in acetonitrile (30 mL) was added 0.2M sodium hydrogen phosphate (30 mL, pH 4.7). After 10 minutes at 35° C., the title D compound from Example 1 dissolved and a vacuum was applied. During the next 65 minutes, solvent was slowly distilled with the aid of a 35° C. warming bath and the volume of the reaction mixture was kept constant with the addition of acetonitrile as required. The pH of the solution was lowered with phosphoric acid and the resulting solution was poured into methylene chloride (60 mL) and shaken. The organic layer was removed and the aqueous layer was extracted with methylene chloride:CH₃CN (2:1, 15 mL). The combined organic layers were dried over anhydrous magnesium sulfate, filtered and concentrated to a white solid which was dried under high vacuum at ambient temperature to give 1.303 g of the title A compound, m.p. 160° C.

Analysis calc'd for $C_{29}H_{31}N_9O_9S_2.1.0-H_2O.0.10CH_3CN.0.015 TFA$ C, 47.66; H, 4.56; N, 17.32; S, 8.71; F, 0.12; Na, 0; KF, 2.40;

Found: C, 47.92; H, 4.34; N, 16.97; S, 8.57; F, 0.12; Na, 0; KF, 2.31.

B.

[3S(Z)]-2-[[[1-(2-Amino-4-thiazolyl)-2-[[1-[[[[3-[[[4,5-bis[[(1,1-dimethylethoxy)carbonyl]oxy]-2-pyridinyl]-carbonyl]amino]-2-oxo-1-imidazolidinyl]sulfonyl]amino]carbonyl]-2-oxo-3-azetidinyl]amino]-2-oxoethylidene]amino]oxy]-2-methylpropanoic acid, diphenylmethyl ester To a solution of the title A compound (1.30 g, 1.82 mmol) in dry dichloromethane (30 ml) at −40° C. under argon was added diisopropylethylamine (0.33 ml, 1.91 mmol). To this solution, via cannula, was added the cold (−40° C.) acid chloride (~1.91 mmol) solution of the title H compound from Example 1. After stirring for 45 minutes at −40° C., the reaction was quenched and worked up by pouring the cold reaction mixture into, and washing with, sodium phosphate buffer (pH 2.0, 0.2M, 2×50 ml). Layer separation was rapid and each aqueous layer was back extracted with dichloromethane (10 ml). The combined organic layers were dried over sodium sulfate, filtered, and reduced in vacuo to an oily solid. The compound was dissolved in ethyl acetate (12 ml) and precipitated by the slow addition of diethyl ether (20 ml) into the rapidly stirred solution, followed by the more rapid addition of ether (60 ml) to complete the precipitation. Filtration, cake rinse (ether) and drying at ambient temperature produced 1.67 g of the title B compound as a finely divided white powder, m.p. 198°–220° C.

C.
2-[[[1-(2-Amino-4-thiazolyl)-2-[[1-[[[[3-[[(1,4-dihydro-5-
-hydroxy-4-oxo-2-pyridinyl)carbonyl]amino]-2-oxo-1-
imidazolidinyl]sulfonyl]amino]carbonyl]-2-oxo-3-
azetidinyl]amino]-2-oxoethylidene]amino]oxy-2-
methylpropanoic acid, disodium salt The procedure from Example 1, part J was used to convert the title B compound to the desired product.

What is claimed is:

1. A process for making a compound of the formula

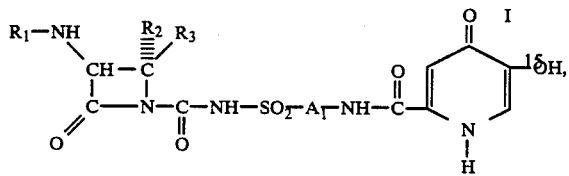

including pharmaceutically acceptable salts thereof, comprising the steps of (a) treating a compound of the formula

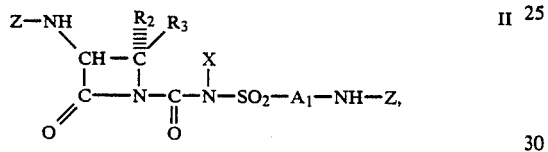

in the presence of a ketonic solvent having the formula

with hydrogen in the presence of a catalyst and thereafter, acylating to provide a compound of the formula

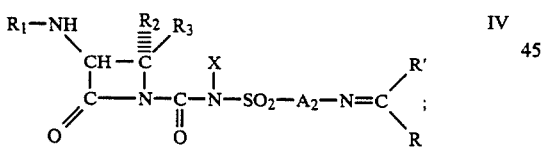

(b) removing the alkylidene or cycloalkylidene group from compound IV and coupling the so-prepared compound with a compound having the formula

wherein Prot is a phenol protecting group, (c) deprotecting the compound formed in step (b) to provide the compounds of formula I:
wherein Z is benzyloxycarbonyl;
X is hydrogen, alkali earth metal or a tri-or tetra-alkylammonium group;
R and R' are each alkyl or R and R' taken together with the carbon atom to which they are attached are a 5-, 6- or 7-membered cycloalkylidene group;
wherein $A_1$ is —HN—,

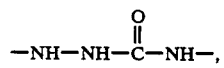

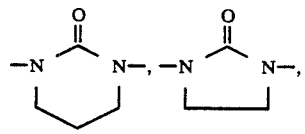

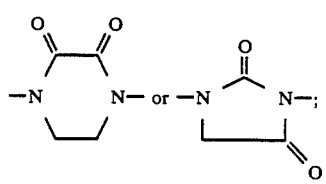

$R_1$ is an acyl group derived from a carboxylic acid; and, $R_2$ and $R_3$ are the same or different and each is hydrogen, alkyl, cycloalkyl, phenyl, substituted phenyl or a 4, 5, 6 or 7-membered heterocycle (hereinafter referred to as $R_x$), or one of $R_2$ and $R_3$ is hydrogen and the other is halomethyl, dihalomethyl, trihalomethyl, alkoxycarbonyl, carboxyl, —CH$_2$X$_1$ (wherein X$_1$ is amino, hydroxy, carboxyl, alkoxycarbonyl, alkanoylamino, phenylcarbonylamino, (substituted phenyl)carbonylamino, alkylsulfonyloxy, phenylsulfonyloxy, (substituted phenyl)sulfonyloxy, phenyl, substituted phenyl cyano,

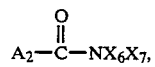

or —O—X$_2$ (wherein A$_2$, X$_2$, X$_6$ and X$_7$ are as hereinafter defined)), or —O—X$_2$ (wherein X$_2$ is alkyl, substituted alkyl, phenyl, substituted phenyl, phenylalkyl, (substituted phenyl)alkyl, alkanoyl, phenylalkanoyl, (substituted phenyl)alkanoyl, phenylcarbonyl, (substituted phenyl)carbonyl, or heteroarylcarbonyl),

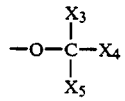

(wherein one of X$_3$ and X$_4$ is hydrogen and the other is hydrogen or alkyl, or X$_3$ and X$_4$ when taken together with the carbon atom to which they are attached form a cycloalkyl group; and X$_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl, (substituted amino) carbonyl, or cyano), or

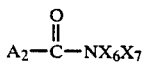

(wherein A₂ is —(CH₂)ₘ—, —(CH₂)ₘ—O—, or —(CH₂)ₘ—NH—, m is 0, 1 or 2, and X₆ and X₇ are the same or different and each is hydrogen, alkyl, phenyl or substituted phenyl, or X₆ is hydrogen and X₇ is amino, substituted amino, alkanoylamino or alkoxy, or X₆ and X₇ when taken together with the nitrogen atom to which they are attached form a 4, 5, 6 or 7-membered heterocycle);

the terms "alkyl" and "alkoxy" refer to both straight and branched chain groups having 1 to 10 carbon atoms;

the terms "cycloalkyl" and "cycloalkenyl" refer to cycloalkyl and cycloalkenyl groups having 3, 4, 5, 6 or 7 carbon atoms;

the term "substituted alkyl" refers to alkyl groups substituted with 1, 2 or 3 azido, amino, halogen, hydroxy, carboxy, cyano, alkoxycarbonyl, aminocarbonyl, alkanoyloxy, alkoxy, phenyloxy, (substituted phenyl)oxy, alkylsulfinyl, or alkylsulfonyl groups;

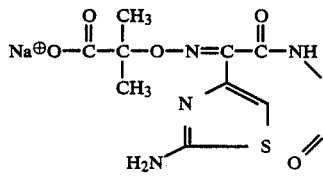

the terms "alkanoyl", "alkenyl", and "alkynyl" refer to both straight and branched chain groups having 2 to 10 carbon atoms;

the terms "halogen" and "halo" refer to fluorine, chlorine, bromine and iodine;

the term "substituted phenyl" refers to a phenyl group substituted with 1, 2 or 3 amino, halogen, hydroxyl, trifluoromethyl, alkyl (of 1 to 4 carbon atoms), alkoxy (of 1 to 4 carbon atoms), alkanoyloxy, aminocarbonyl, or carboxy groups;

the expression "a 4, 5, 6 or 7-membered heterocycle" refers to substituted and unsubstituted, aromatic and non-aromatic heterocycle groups, wherein each may contain 1, 2 or 3 nitrogen or oxygen atoms and wherein substituents are selected from oxo, halogen, hydroxy, nitro, amino, cyano trifluoromethyl, alkyl of 1 to 4 carbons, alkoxy of 1 to 4 carbons, alkylsulfonyl, phenyl, substituted phenyl 2-furfurylideneamino benzylideneamino and substituted alkyl groups wherein the alkyl group has 1 to 4 carbons, wherein said aromatic groups are selected from pyridinyl, furanyl, pyrrolyl, 1,2,3-triazolyl, 1,2,4-triazolyl, imidazolyl, pyrimidinyl, oxazolyl, triazinyl, and tetrazolyl; and said nonaromatic groups are selected from azetidinyl, oxetanyl, piperidinyl, piperazinyl, imidazolidinyl, oxazolidinyl, pyrrolidinyl, tetrahydropyrimidinyl and hexahydroazepinyl.

2. A process of claim 1 wherein X is a tri-or tetra-alkylammonium group.

3. A process of claim 2 wherein X is a tetrabutylammonium group.

4. A process of claim 1 wherein said ketonic solvent is selected from acetone, diethyl ketone and methylethyl ketone.

5. A process of claim 4 wherein said ketonic solvent is acetone.

6. A process of claim 1 wherein R₁ is

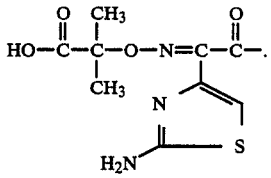

7. A process of claim 1 wherein A₁ is

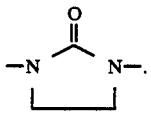

8. A process of claim 1 wherein R₂ and R₃ are each hydrogen.

9. A process of claim 1 wherein the compound of formula I is

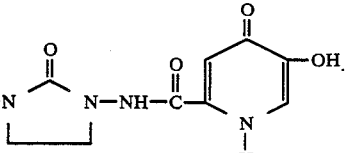

10. A process of claim 1 wherein the compounds of formula II are prepared by treating a compound of the formula

with a nitrosating reagent, followed by reduction and reaction with a compound of the formula halogen—Z followed by treatment with an acid to provide a compound of the formula

which is reacted with a compound of the formula

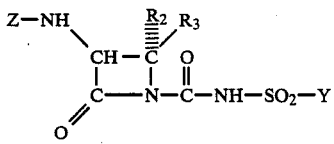

wherein Y is a leaving group, in the presence of a tertiary alkylamine and a solvent to provide compounds of formula II wherein X is hydrogen or an alkaline earth metal; and, treating a so-formed compound with a tri- or tetraalkylammonium sulfate to provide compounds of formula II wherein X is a tri- or tetra-alkylammonium group.

11. A process of claim 10 wherein said nitrosating reagent is sodium nitrite in aqueous sulfuric acid.

12. A process of claim 10 wherein said reduction is carried out by treatment with zinc.

13. A process of claim 10 wherein said acid is hydrochloric.

14. A process of claim 10 wherein said tertiary alkylamine is selected from triethylamine and diisopropylethylamine.

* * * * *